United States Patent
Umekawa

(10) Patent No.: US 9,480,395 B2
(45) Date of Patent: Nov. 1, 2016

(54) OPHTHALMIC DEVICE, CONTROL METHOD, AND NON-TRANSITORY COMPUTER READABLE MEDIUM

(71) Applicant: CANON KABUSHIKI KAISHA, Tokyo (JP)

(72) Inventor: Kazuaki Umekawa, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 206 days.

(21) Appl. No.: 14/253,667

(22) Filed: Apr. 15, 2014

(65) Prior Publication Data

US 2014/0313485 A1    Oct. 23, 2014

(30) Foreign Application Priority Data

Apr. 17, 2013  (JP) .................................. 2013-086878

(51) Int. Cl.
| | |
|---|---|
| *A61B 3/10* | (2006.01) |
| *A61B 3/00* | (2006.01) |
| *A61B 3/103* | (2006.01) |
| *A61B 3/107* | (2006.01) |
| *A61B 3/117* | (2006.01) |
| *A61B 3/14* | (2006.01) |

(52) U.S. Cl.
CPC ........... *A61B 3/1025* (2013.01); *A61B 3/0008* (2013.01); *A61B 3/103* (2013.01); *A61B 3/107* (2013.01); *A61B 3/102* (2013.01); *A61B 3/1005* (2013.01); *A61B 3/1173* (2013.01); *A61B 3/14* (2013.01)

(58) Field of Classification Search
CPC ...... A61B 3/103; A61B 3/1208; A61B 3/14; A61B 3/12
USPC .................. 351/200, 205, 206, 211, 246
See application file for complete search history.

(56) References Cited

U.S. PATENT DOCUMENTS

| | | | | |
|---|---|---|---|---|
| 5,500,697 | A | * | 3/1996 | Fujieda ......................... 351/212 |
| 2009/0103050 | A1 | * | 4/2009 | Michaels et al. ............. 351/208 |
| 2012/0218518 | A1 | | 8/2012 | Wada |
| 2013/0162945 | A1 | | 6/2013 | Tanaami |
| 2014/0028977 | A1 | | 1/2014 | Umekawa et al. |
| 2014/0313485 | A1 | | 10/2014 | Umekawa |

FOREIGN PATENT DOCUMENTS

| | | |
|---|---|---|
| EP | 2692283 A1 | 2/2014 |
| JP | 3576656 B2 | 10/2004 |

OTHER PUBLICATIONS

Carl Zeiss Meditec IOL Master, IOLMaster—Keratometer Tips, Doctor-Hill.com, http://www.doctor-hill.com/iol-master/ker-tips. html, URL: http://www.archive.org am Nov. 23, 2010.

* cited by examiner

*Primary Examiner* — James Greece
(74) *Attorney, Agent, or Firm* — Canon USA, Inc. I.P. Division

(57) ABSTRACT

Provisioned is a selecting unit configured to select a bright spot image corresponding to a reflected light beam reflected by the cornea of the subject eye from among a plurality of bright spot images on the basis of a positional relationship between a first bright spot image formed from a plurality of bright spot images corresponding to a first light beam in a first direction and a second bright spot image corresponding to a second light beam in a second direction different than the first direction, and a calculating unit configured to calculate a state of alignment between the subject eye and a measuring unit using the bright spot image selected from the first bright spot images.

22 Claims, 9 Drawing Sheets

OPHTHALMIC DEVICE, CONTROL METHOD, AND NON-TRANSITORY COMPUTER READABLE MEDIUM

BACKGROUND OF THE INVENTION

1. Field of the Invention

The present invention relates to an ophthalmic device, and a control method and program thereof. More particularly, the present invention relates to an ophthalmic device configured to measure characteristics of a subject eye and photograph the subject eye, a control method for the ophthalmic device, and a program to control the ophthalmic device.

2. Description of the Related Art

Using ophthalmic devices which measure the characteristics of a subject eye, to perform auto-alignment to obtain alignment between the subject eye and the optical system of the device by projecting a light beam onto the cornea of the subject eye, and detecting the reflected image by a light-receiving element, is known.

For example, Japanese Patent Publication No. 3576656 discloses an alignment method for an ophthalmic device in which positional information of the three-dimensional direction between the subject eye and the optical system of the device is detected from the positional relationship of the reflected image separated and received by a pair of light deflection members.

Now, an operation is performed for patients with cataracts to insert an intraocular lens (IOL, also called an "artificial lens") in place of the crystalline lens.

SUMMARY OF THE INVENTION

However, the refractive index of the IOL is higher than that of the crystalline lens, and the light beam projected onto the cornea is reflected as the IOL reflected light. For this reason, according to the method of the related art, there have been problems in which IOL reflection ghosts are falsely detected as the actual reflected image for alignment. Because of such problems, auto-alignment may not complete successfully in ophthalmic devices that have an auto-alignment function, for example. When auto-alignment cannot be performed, the examiner has to align the device manually to take measurements, which requires more measurement time.

It has been found desirable to provide an ophthalmic device and an alignment method for ophthalmic devices in which actual reflected images for alignment that are not IOL reflection ghosts are correctly selected for subject eyes that have the IOL.

The present invention includes a measuring unit configured to measure information of a subject eye, a first projecting unit configured to project a light beam onto the subject eye in a first direction, a second projecting unit configured to project a light beam onto the subject eye from a second direction different than the first direction of the first projecting unit, a selecting unit configured to select a bright spot image corresponding to a reflected light beam reflected by the cornea of the subject eye from among a plurality of bright spot images on the basis of a positional relationship between a first bright spot image formed from a plurality of bright spot images corresponding to the light beam projected by the first projecting unit and a second bright spot image corresponding to the light beam projected from the second projecting unit, and a calculating unit configured to calculate a state of alignment between the subject eye and a measuring unit using the bright spot image selected from the first bright spot images.

Further features of the present invention will become apparent from the following description of exemplary embodiments with reference to the attached drawings.

DESCRIPTION OF THE EMBODIMENTS

Hereinafter, the present invention will be described in detail based on an embodiment in the figures. The following embodiment exemplifies an ophthalmic device as an eye refractometer 1 configured to measure eye refraction information.

Overall Configuration of the Device

Figure 1:
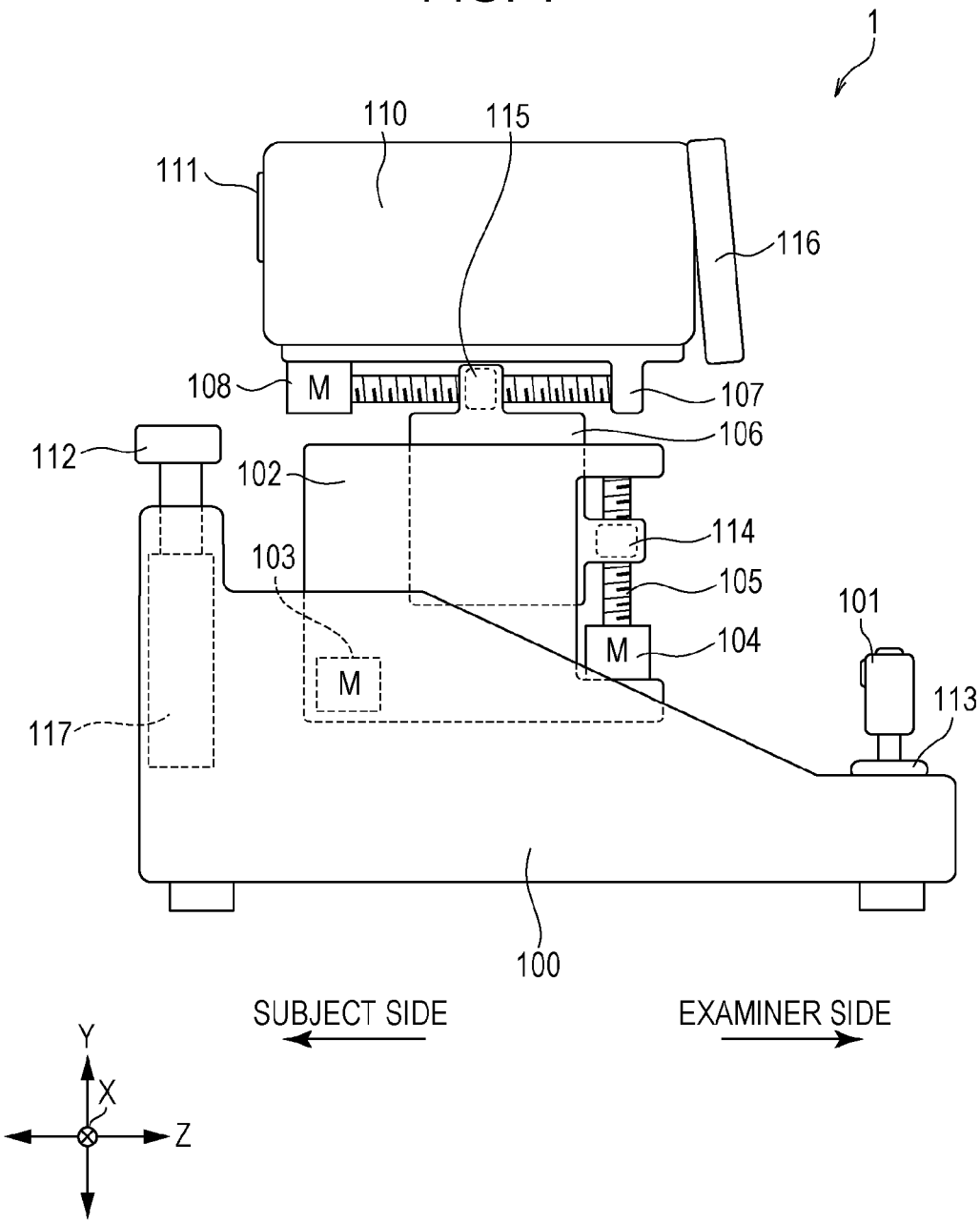
FIG. 1 is an external view of an eye refractometer related to an embodiment of the present invention.

First, the overall configuration of the eye refractometer 1 related to the embodiment of the present invention will be described with reference to FIG. 1. FIG. 1 is a schematic diagram illustrating a configuration diagram of the eye refractometer 1 configured to measure eye refraction information as the ophthalmic device related to the present embodiment.

The eye refractometer 1 related to the embodiment of the present invention includes a base 100, an X-axis drive frame 102, a Y-axis drive frame 106, a Z-axis drive frame 107, and a measuring unit 110.

The X-axis drive frame 102 is movable horizontally (direction perpendicular to the paper surface, hereinafter, the X-axis direction) in relation to the base 100. An X-axis direction drive mechanism, which is an example of a driving unit, in the X-axis drive frame 102 is configured with an X-axis drive motor 103, an X-axis feed screw (not illustrated), and an X-axis feed nut (not illustrated). The X-axis drive motor 103 is fixed to the base 100. The X-axis feed screw is coupled to the output shaft of the X-axis drive motor 103. The X-axis feed nut is fixed to the X-axis drive frame 102, and can move the X-axis feed screw in the X-axis direction. The X-axis feed screw rotates by the rotation of the output shaft of the X-axis drive motor 103, and the X-axis drive frame 102 moves in the X-axis direction together with the X-axis feed nut.

The Y-axis drive frame 106 is movable vertically (direction vertical to the paper surface, hereinafter, the Y-axis direction) in relation to the X-axis drive frame 102. A Y-axis direction drive mechanism, which is an example of a driving unit, in the Y-axis drive frame 106 is configured with a Y-axis drive motor 104, a Y-axis feed screw 105, and a Y-axis feed nut 114. The Y-axis drive motor 104 is fixed to the X-axis drive frame 102. The Y-axis feed screw 105 is coupled to the output shaft of the Y-axis drive motor 104. The Y-axis feed nut 114 is fixed to the Y-axis drive frame 106, and can move the Y-axis feed screw 105 in the Y-axis direction. The Y-axis feed screw 105 rotates by the rotation of the output shaft of the Y-axis drive motor 104, and the Y-axis drive frame 106 moves in the Y-axis direction together with the Y-axis feed nut 114.

The Z-axis drive frame 107 is movable longitudinally (left-right direction on the paper surface, hereinafter, the Z-axis direction) in relation to the Y-axis drive frame 106. A Z-axis direction drive mechanism, which is an example of a driving unit, in the Z-axis drive frame 107 is configured with a Z-axis drive motor 108, a Z-axis feed screw 109, and a Z-axis feed nut 115. The Z-axis drive motor 108 is fixed to the Z-axis drive frame 107. The Z-axis feed screw 109 is coupled to the output shaft of the Z-axis drive motor 108. The Z-axis feed nut 115 is fixed to the Y-axis drive frame 106, and can move in the Z-axis direction relative to the Z-axis feed screw 109. The Z-axis feed screw 109 rotates by the rotation of the output shaft of the Z-axis drive motor 108, and the Z-axis drive frame 107 moves in the Z-axis direction together with the Z-axis drive motor 108 and the Z-axis feed screw 109.

The measuring unit 110 is fixed to the top of the Z-axis drive frame 107. The measuring unit 110 functions as an obtaining unit to obtain the eye refraction, which is one part of the unique information for subject eye E.

A light source unit 111 configured to serve as a light source (not illustrated) for alignment and to measure corneal curvature is installed to the end of the measuring unit 110 on the subject eye side.

An LCD monitor 116 is installed to the end of the measuring unit 110 on the examiner side. The LCD monitor 116 is a display member configured to monitor the subject eye E. The LCD monitor 116 can display images of the subject eye E and measurement results.

A joystick 101 is installed to the end of the base 100 on the examiner side. The joystick 101 is an operation member configured to align the measuring unit 110 with the subject eye E (alignment). During measurement, the examiner can adjust the position of the measuring unit 110 by tilting the joystick 101.

When measuring the eye refraction, the subject rests the chin on a chinrest 112, and rests the forehead against a forehead rest portion on the face rest frame (not illustrated) fixed to the base 100 to secure the position of the subject eye E. The position of the chinrest 112 is adjustable in the Y-axis direction by a chinrest drive mechanism 113.

Measuring Unit

Figure 2:
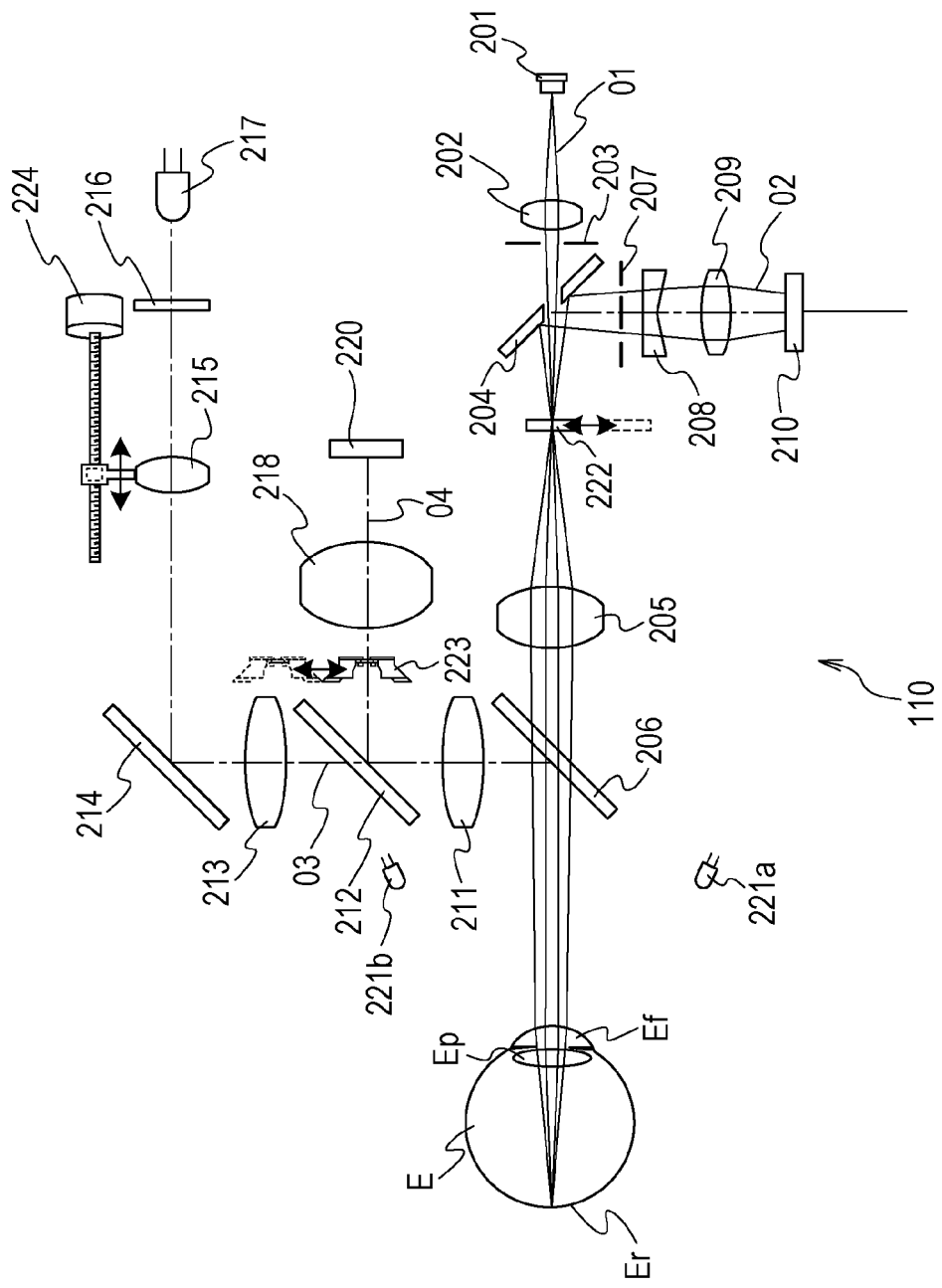
FIG. 2 is a layout view of an optical system in a measuring unit regarding the embodiment illustrated in FIG. 1.

Next, the configuration of the measuring unit 110 will be described with reference to FIG. 2. FIG. 2 is a schematic diagram illustrating the configuration of the measuring unit 110, and mainly is a layout view illustrating the internal optical system.

An optical system for measuring eye refraction, a fixation target projecting optical system, and an alignment light-receiving optical system are arranged in the measuring unit 110. The alignment light-receiving optical system is used for both observation of the anterior ocular segment of the subject eye E and alignment detection.

The configuration of the optical system for measuring eye refraction is described next. An eye refraction measuring light source 201, which is an example of a first projecting unit, is a light source configured to project a light beam having a wavelength of 880 nm (first light beam) to a predetermined portion of the subject eye E. A projecting lens 202, a diaphragm 203, an apertured mirror 204, a lens 205, and a dichroic mirror 206 are arranged in this order along an optical path 01 extending from the eye refraction measuring light source 201 to the subject eye E. The diaphragm 203 is disposed nearly conjugate to a pupil Ep of the subject eye E. The lens 205 functions as a projecting unit. The dichroic mirror 206 reflects all visible light and infrared light having a wavelength of less than 880 nm from the subject eye E side, and reflects a portion of the light beam having a wavelength of at least 880 nm.

A diaphragm 207, a light beam spectroscopic prism 208, a lens 209, and an imaging device 210 are arranged in this order along an optical path 02 in the reflected direction of the apertured mirror 204. The diaphragm 207 is provisioned with an annular slit, and is disposed nearly conjugate with the pupil Ep.

The light beam emitted by the eye refraction measuring light source 201 is focused by the diaphragm 203, and is subjected to primary imaging in front of the lens 205 by the projecting lens 202. The light beam passes through the lens 205 and the dichroic mirror 206, and is then projected into the pupil center of the subject eye E.

The projected light beam is reflected by a fundus Er, and this reflected light beam (fundus reflected light beam) passes through the pupil center to again enter the lens 205. After passing through the lens 205, the reflected light beam is reflected near the apertured mirror 204.

The light beam reflected near the apertured mirror 204 is pupil-separated by the light beam prism spectroscopic 208 and the diaphragm 207, which is nearly conjugate to the pupil Ep of the subject eye E, and then projected as a ring image to the light-receiving surface of the imaging device 210.

The imaging device 210 images the projected ring image.

If the subject eye E has normal vision, the projected ring image will form a predetermined circle. For eyes with myopia, the ring image circle is smaller than that of eyes with normal vision. For eyes with hyperopia, the ring image circle is larger than that for eyes with normal vision.

For subject eyes E with astigmatism, the ring images forms an ellipse, and the angle formed by the horizontal axis and the ellipse is the astigmatism axial angle. A system control unit 401 (described later) obtains the eye refraction on the basis of the coefficient from this ellipse.

Conversely, a fixation target projecting optical system and an alignment light-receiving optical system are arranged along the reflected direction of the dichroic mirror 206.

A lens 211, a dichroic mirror 212, a lens 213, a reflecting mirror 214, a lens 215, a fixation target 216, and a fixation target lighting light source 217 are arranged in this order along an optical path 03 of the fixation target projecting optical system.

The fixation target lighting light source 217 lights during fixation guidance. The projected light beam emitted by the fixation target lighting light source 217 lights the fixation target 216 from the rear. The light beam that has passed through the fixation target 216 is projected to the fundus Er of the subject eye E via the lens 215, the reflecting mirror 214, the lens 213, the dichroic mirror 212, and the lens 211.

The lens 215 is movable in the optical axis direction by a fixation target guidance motor 224. As a result, the lens 215 performs diopter guidance for the subject eye E, enabling a fogging state to be achieved.

An alignment prism diaphragm 223, which is an example of a deflector, an imaging lens 218, and an imaging device 220 are arranged in this order along an optical path 04 in the reflecting direction of the dichroic mirror 212. The alignment prism diaphragm 223 is inserted onto and removed from the optical path 04 by an alignment prism diaphragm insertion and removal solenoid (not illustrated). When the alignment prism diaphragm 223 is on the optical path 04, alignment can be performed, and when removed from the optical path, anterior ocular segment observation or transillumination observation can be performed.

Figure 3:
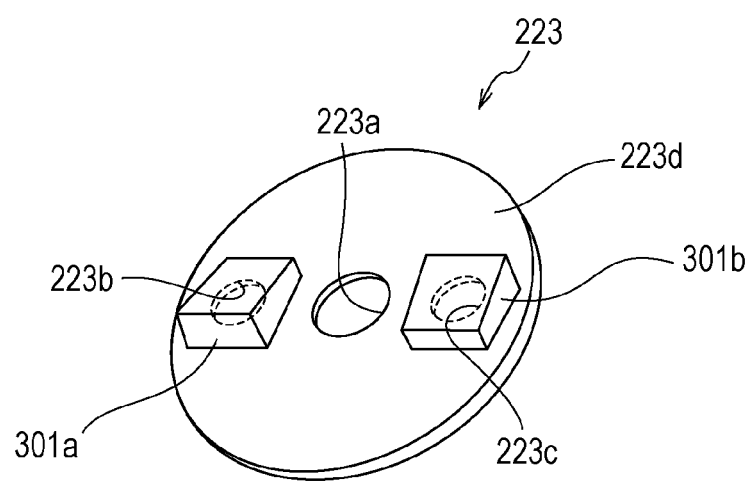
FIG. 3 is a perspective view of an alignment prism diaphragm.

The configuration of the alignment prism diaphragm 223 will now be described with reference to FIG. 3. FIG. 3 is a diagram schematically illustrating the form of the alignment prism diaphragm 223. Three openings 223a, 223b, and 223c are formed in a disc-shaped aperture plate 223d so as to line up serially. Alignment prisms 301a and 301b which transmit only light beams having wavelengths around 880 nm are attached to the dichroic mirror 212 side of the openings 223b and 223c at either side.

Returning to FIG. 2, anterior ocular segment lighting light sources 221a and 221b having wavelengths around 780 nm, which are a second projecting unit, are arranged diagonally forward to the anterior ocular segment of the subject eye E. The anterior ocular segment lighting light sources 221a and 221b project light beams of the aforementioned wavelength (second light beam) to the anterior ocular segment of the subject eye E. The term "light beam" includes all light that is not completely diffused. The anterior ocular segment lighting light sources 221a and 221b can project light beams from a direction different than that of the optical path 01 (light axis of light beams from the eye refraction measuring light source 201) extending from the eye refraction measuring light source 201 to the subject eye E in relation to the subject eye E. The two anterior ocular segment lighting light sources 221a and 221b are provisioned in positions symmetrical with respect to the optical path 01 extending from the eye refraction measuring light source 201 to the subject eye E. The two anterior ocular segment lighting light sources 221a and 221b can project light beams to two locations symmetrical with respect to light beams projected from the eye refraction measuring light source 201, which are the corneas of the subject eye E. The reflected light beam from the subject eye E reaches the surface of the light-receiving sensor of the imaging device 220 via the dichroic mirror 206, the lens 211, the dichroic mirror 212, and the opening 223a in the center of the alignment prism diaphragm 223. The imaging device 220 forms an image of the anterior ocular segment of the subject eye E by detecting the reflected light beam that has arrived.

The light source for alignment detection is also used as the eye refraction measuring light source 201. During alignment, a semi-transparent diffusion plate 222 is inserted onto the optical path 01 by a diffusion plate insertion and removal solenoid (not illustrated).

The position where the diffusion plate 222 is inserted is nearly the primary imaging position of the projecting lens 202 in the eye refraction measuring light source 201, and the focus position of the lens 205. As a result, the light beam from the eye refraction measuring light source 201 is imaged once on the diffusion plate 222, and then becomes a secondary light source. The light from this secondary light source heads toward the subject eye E from the lens 205 becoming a thick parallel light beam, and is then projected onto the subject eye E.

This parallel light beam is reflected by a cornea Ef of the subject eye E. This reflected light beam forms a bright spot image. A portion of this reflected light beam is reflected by the dichroic mirror 206, and then reflected by the dichroic mirror 212 through the lens 211. This reflected light beam passes through the openings 223b and 223c in the alignment prism diaphragm 223, and the alignment prisms 301a and 301b. The light beam that has passed through the alignment prism 301a is refracted downward (deflected), and the light beam that has passed through the alignment prism 301b is refracted upward (deflected). These refracted light beams are converged by the imaging lens 218 being formed into an image by the imaging device 220.

The opening 223a in the center of the alignment prism diaphragm 223 is configured to pass light beams having wavelengths of at least 780 nm from the anterior ocular segment lighting light sources 221a and 221b. Thus, the light beam illuminated by the anterior ocular segment lighting light sources 221a and 221b and reflected by the anterior ocular segment follows a path similar to the path of the light beam reflected by the cornea Ef, passing through the opening 223a in the alignment prism diaphragm 223 and being formed into an image on the imaging device 220 by the imaging lens 218.

The imaging device 220 images an image that includes the imaged light beams (bright spot image). The system control unit 401 (described later) detects the position of the light beam (bright spot image) included in the imaged image. The system control unit 401 (described later), which is an example of an auto-alignment unit, can perform auto-alignment of the subject eye E by the positional relationship with the light beam via these diaphragms.

System Configuration

Figure 4:
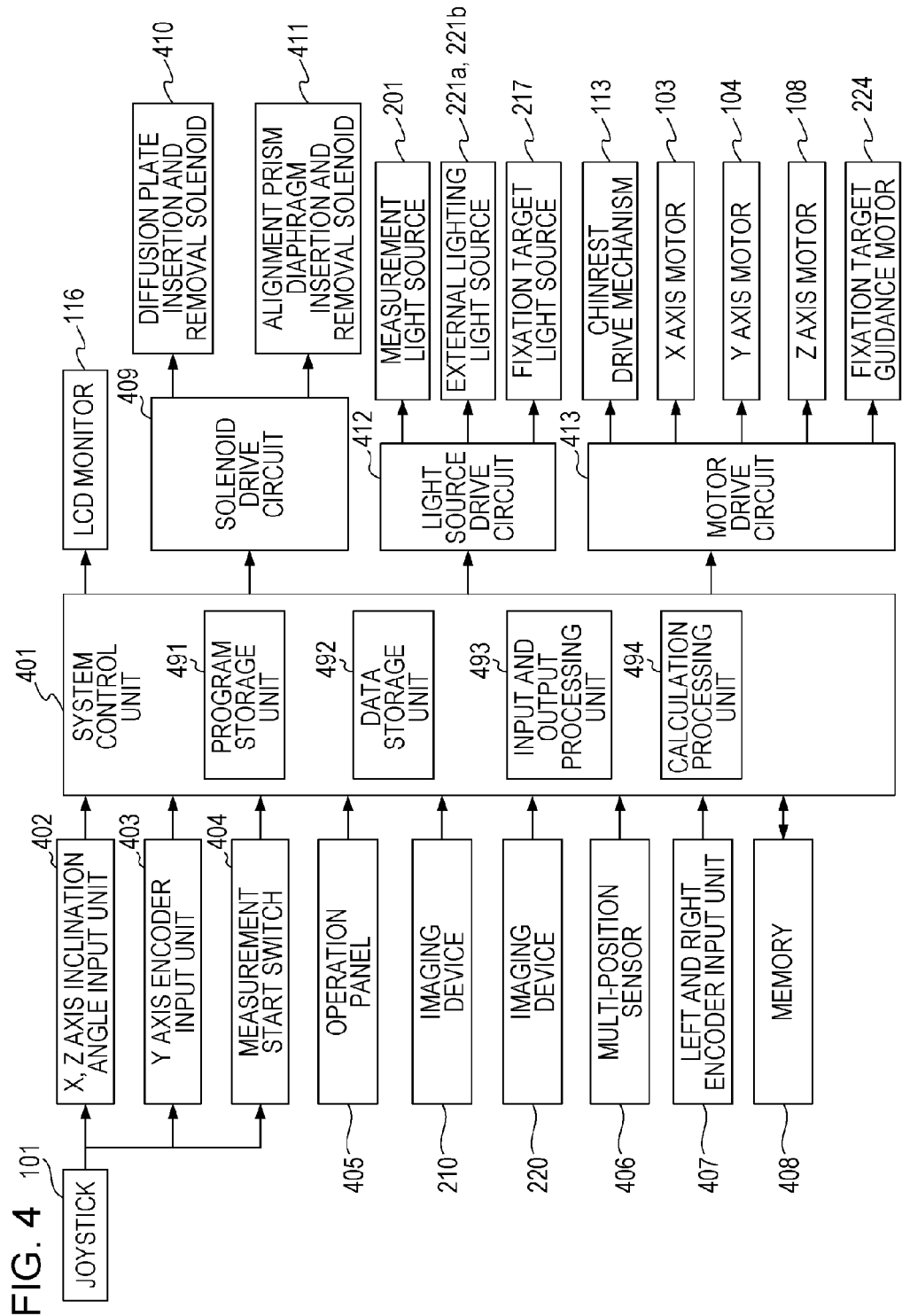
FIG. 4 is a system block diagram of the eye refractometer related to an embodiment of the present invention.

Next, the system configuration of the eye refractometer 1 will be described with reference to FIG. 4. FIG. 4 is a system block diagram of the eye refractometer 1.

The system control unit 401 controls the entire system. The system control unit 401 includes a program storage unit 491, a data storage unit 492, an input and output control unit 493, and a calculation processing 494. A computer program in a computer-readable format for controlling the eye refractometer 1 is stored in the program storage unit 491. Data for correcting the eye refraction value, etc. is stored in the data storage unit 492. The input and output control unit 493 controls input and output between various devices. The calculation processing 494 reads and executes the computer program stored in the program storage unit 491. As a result, control of each unit and predetermined processing is performed on data obtained from each unit (for example, images taken by the imaging devices 210 and 220).

An inclination angle input unit 402 detects forward, backward, left, and right inclination angles when the joystick 101 is operated, and transmits these angles to the system control unit 401. A Y axis encoder input unit 403 detects the rotational angle when the joystick 101 is operated, and transmits these angles to the system control unit 401. A measurement start switch 404 is an operation member that operates to start measuring. The measurement start switch 404 transmits signals to the measurement start switch 404 in response to being operated. The examiner can perform auto-alignment of the measuring unit 110 and the operation to start measuring by using the joystick 101.

A print switch, chinrest vertical movement switches, etc. are disposed on an operation panel 405 arranged to the base 100. When these switches are operated, signals are transmitted to the system control unit 401 in response to the operated switch.

The imaging device 220 transmits anterior ocular segment images of the subject eye E to the system control unit 401. The imaging device 210 transmits ring images for imaged eye refraction calculations to the system control unit 401.

Memory 408 stores anterior ocular segment images of the subject eye E imaged by the imaging device 220, ring images for eye refraction calculations imaged by the imaging device 210, and other types of data.

The system control unit 401 extracts the pupil image of the subject eye E and the cornea reflection image from the images stored in the memory 408, and performs the alignment detection. The system control unit 401 synthesizes text and graphical data into the anterior ocular segment image of the subject eye E imaged by the imaging device 220.

The LCD monitor 116 displays the anterior ocular segment image, measurement values, etc. in accordance with the control from the system control unit 401.

A solenoid drive circuit 409 drives a diffusion plate insertion and removal solenoid 410 and an alignment prism diaphragm insertion and removal solenoid 411 in accordance with control from the system control unit 401.

A motor drive circuit 413 drives the X-axis drive motor 103, the Y-axis drive motor 104, the Z-axis drive motor 108, the motor in the chinrest drive mechanism 113, and the fixation target guidance motor 224 in accordance with the control from the system control unit 401.

A light source drive circuit 412 turns on/off and changes the amount of light of the eye refraction measuring light source 201, the anterior ocular segment lighting light sources 221a and 221b, and the fixation target lighting light source 217 in accordance with the control from the system control unit 401.

Operation of the Eye Refractometer

The operation of the eye refractometer 1 provisioned with a configuration as described beforehand will now be described.

Figure 5A:
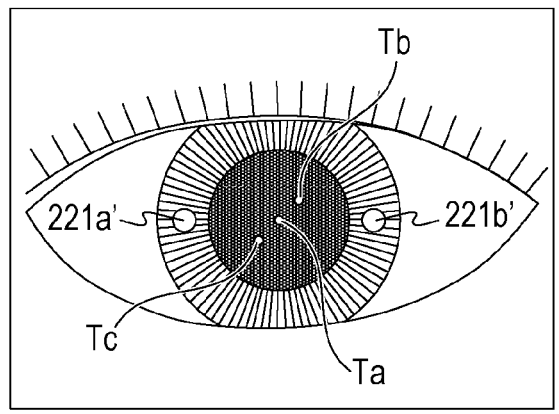
FIGS. 5A through 5C are descriptive views of an anterior ocular segment image during cornea bright spot auto-alignment.
Figure 5B:
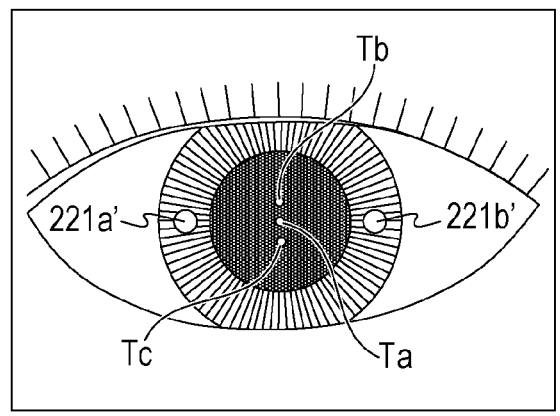
Figure 5C:
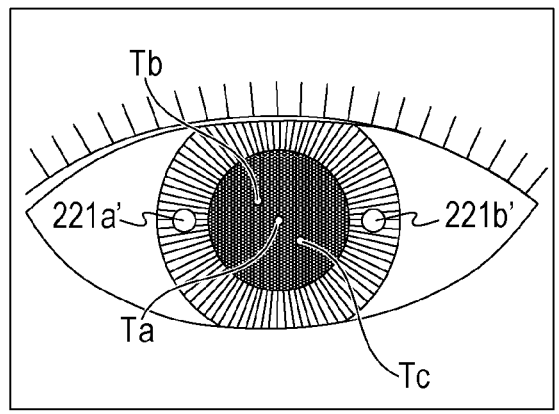

First, the auto-alignment operation will be described with reference to FIGS. 5A through 5C. FIGS. 5A through 5C are diagrams schematically illustrating the anterior ocular segment image during auto-alignment.

During auto-alignment as illustrated in FIGS. 5A through 5C, the system control unit 401 turns on the eye refraction measuring light source 201 and the anterior ocular segment lighting light sources 221a and 221b via the light source drive circuit 412.

The light beam projected from the eye refraction measuring light source 201 is reflected by the cornea Ef. The cornea bright spot image from the reflected light beam corresponding to this light beam is imaged by the imaging device 220 as index images Ta, Tb, and Tc (first bright spot image). That is to say, the light beam (cornea bright spot image) divided by the openings 223a, 223b, and 223c in the alignment prism diaphragm 223 and the alignment prisms 301a and 301b is formed into the index images Ta, Tb, and Tc by the imaging device 220.

The light beams projected from the anterior ocular segment lighting light sources 221a and 221b are reflected by the cornea Ef of the subject eye E. Bright spot images 221a' and 221b' (second bright spot image) from the reflected light beam corresponding to this light beam is imaged by the imaging device 220 together with the anterior ocular segment of the subject eye E onto which light has been illuminated onto by the anterior ocular segment lighting light sources 221a and 221b.

Therefore, as illustrated in FIGS. 5A through 5C, index images Ta, Tb, and Tc from the cornea bright spot image and the bright spot images 221a' and 221b' from the anterior ocular segment lighting light sources 221a and 221b are reflected in the anterior ocular segment imaged by the imaging device 210.

The system control unit 401 calculates the state of alignment from the anterior ocular segment image imaged by the imaging device 210. The system control unit 401 performs auto-alignment of the measuring unit 110 on the basis of the calculated state of alignment so that a proper state of alignment is achieved. The state of alignment is also called the state of the positional relationship between the optical system of the measuring unit 110 and the subject eye E. The proper state of alignment is the state in which the light axis of the optical path 01 matches the center of the cornea Ef of the subject eye E in relation to the X-axis and Y-axis directions. Regarding the Z-axis direction, the proper state also refers to the distance from the measuring unit 110 to the subject eye E is in a state in which the distance is suitable for imaging the subject eye E. This distance is determined according to the configuration of the optical system in the measuring unit 110 (for example, the configuration of the diaphragm 203). FIGS. 5A through 5C are diagrams illustrating schematically the relationship between the state of alignment and the three index images Ta, Tb, and Tc. As illustrated in FIGS. 5A through 5C, when the position is suitable in relation to the X-axis direction and the Y-axis direction (the state of alignment in relation to the X- and Y-axis directions is proper), the center index image Tb is positioned to the center of the cornea Ef of the subject eye E. As illustrated in FIG. 5B, when the distance between the measuring unit 110 and the subject eye E is proper (the state of alignment in relation to the Z-axis direction is proper), the three index images Ta, Tb, and Tc line up in series vertically.

That is to say, the alignment prism diaphragm 223 divides the reflected light beam from the subject eye E into three light beams deflected in different directions. The alignment prism diaphragm 223 is configured so that the three index images Ta, Tb, and Tc line up vertically when the distance between the measuring unit 110 and the subject eye E is the proper distance for observing the subject eye E.

During auto-alignment, the system control unit 401 detects the three index images Ta, Tb, and Tc reflected in the anterior ocular segment image. The system control unit 401 calculates the direction of deviation and the amount of deviation between the center index image Ta and the cornea Ef of the subject eye E after detecting the three index images Ta, Tb, and Tc. Next, the system control unit 401 controls the motor drive circuit 413 to move the measuring unit 110 vertically and horizontally (X- and Y-axis directions) toward the position where the center of the index image Ta is in the center of the cornea Ef (where the amount of deviation is zero). The system control unit 401 stops moving the measuring unit 110 vertically and horizontally after the center index image Ta is positioned to the center of the cornea Ef.

The system control unit 401 then calculates the state of alignment in relation to the Z-axis direction of the measuring unit 110 from the X-axis coordinates from the upper and lower two index images Tb and Tc. That is to say, the system control unit 401 calculates the difference in the X-axis coordinates between the two index images Tb and Tc, and then calculates the amount of deviation from the proper position of the measuring unit 110 from the size of this difference and whether it is positive or negative. FIG. 5A illustrates the anterior ocular segment image when the state of alignment not acceptable because the measuring unit 110 is too far from the subject eye E. FIG. 5C illustrates the anterior ocular segment image when the state of alignment not acceptable because the measuring unit 110 is too close from the subject eye E. As illustrated in FIGS. 5A and 5C, when the measuring unit 110 is either too close to or too far from the subject eye E, the two index images Tb and Tc deviate relative to the X-axis direction. Whether the deviation is a positive or negative value depends if the measuring unit 110 is either too close to or too far from the proper state in relation to the subject eye E. The relative amount of deviation also varies depending on the distance from the proper state. The system control unit 401 then controls the motor drive circuit 413 to drive the measuring unit 110 in longitudinally (Z-axis direction) so that the relative amount of deviation between the two index images Tb and Tc is zero (the three index images Ta, Tb, and Tc line up vertically).

As illuminated in FIG. 5B, the system control unit 401 completes the auto-alignment operation when the state in which the center index image Ta is positioned to the center of the cornea Ef of the subject eye E, and the three index images Ta, Tb, and Tc line up as one row vertically.

In this way, the system control unit 401 uses the results of detecting the positions of the index images Ta, Tb, and Tc to calculate the state of alignment and perform auto-alignment based on the calculation results.

According the aforementioned description, the illustrated configuration executes auto-alignment using the calculated state of alignment, but the configuration may be different from this. For example, the system control unit 401 may display the calculated state of alignment on the LCD monitor 116. For example, the distance from the current position of the measuring unit 110 to the position at which the proper state is achieved may be disposed as the state of alignment. An arrow illustrating the direction of movement from the current position of the measuring unit 110 to the proper state of alignment may also be displayed. The system control unit 401 may also perform auto-alignment while displaying the state of alignment on the LCD monitor 116.

The operation to measure the eye refraction will be described next.

When measuring the eye refraction, the system control unit 401 removes the diffusion plate 222 inserted onto the optical path 01 for auto-alignment from the optical path 01. The system control unit 401 controls the light source drive circuit 412 to adjust the amount of light from the eye refraction measuring light source 201, and projects the measurement light beam to the fundus Er of the subject eye E.

The reflected light beam from the fundus Er (fundus image) follows the optical path 02 reaching the imaging device 210. The fundus image is projected to the imaging device 210 in a ring form by the eye refraction of the subject eye E and the diaphragm 207. The imaging device 210 images the fundus image projected in a ring form (ring image). The imaged ring image is stored in the memory 408.

The system control unit 401 calculates the center of gravity coordinates for the ring image of the fundus image stored in the memory 408, and obtains equation for the ellipse. The system control unit 401 calculates the major axis, minor axis, and inclination of the major axis for the obtained ellipse, and then calculates the eye refraction value as the so-called preliminary measurement of the subject eye E. This preliminary measurement is used to determine if the subject eye E has myopia or hyperopia.

The system control unit 401 references the obtained eye refraction value, and moves the lens 215 to the position corresponding to this eye refraction value. As a result, the system control unit 401 presents the fixation target 216 to the subject eye E at the refractive index corresponding to the refractive index of the subject eye E.

Afterwards, the system control unit 401 moves the lens 215 for a predetermined distance, fogs the fixation target 216, and lights the eye refraction measuring light source 201 again to measure the eye refraction.

The system control unit 401 moves the lens 215 by controlling the motor drive circuit 413 to drive the fixation target guidance motor 224.

In this way, the system control unit 401 measures the eye refraction, fogs the fixation target 216, and repeats the measurement of the eye refraction. As a result, a stable final measurement of the eye refraction can be obtained.

Index Image Selection

Next, the method to select the bright spot image in which the cornea bright spot image (index image) is not ghosting when the subject eye E has an IOL implant (artificial lens has been implanted) will be described.

Figure 6:
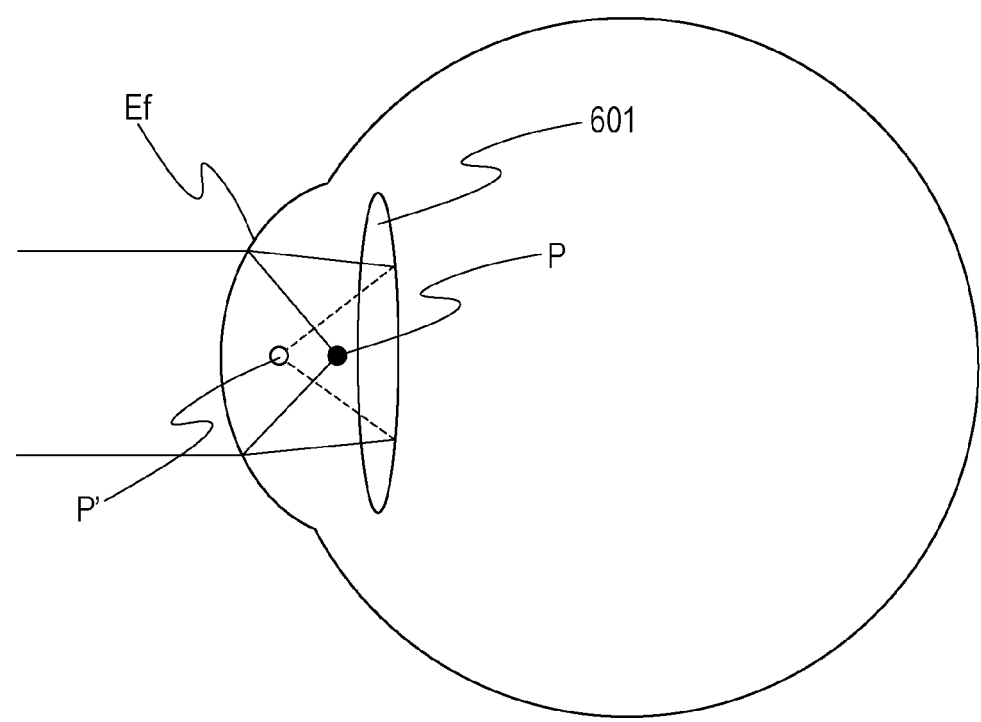
FIG. 6 is a diagram illustrating the cornea bright spot in an IOL-implanted eye.

FIG. 6 is a diagram illustrating the cornea bright spot image for an IOL-implanted eye. Light reflected by the cornea Ef forms a virtual image P by these corneal reflections. A real image P' reflected by IOL 601 is formed from projected light beams that were not reflected by the cornea Ef. The actual image P' is formed closer to the cornea Ef than the virtual image P.

Figure 7:
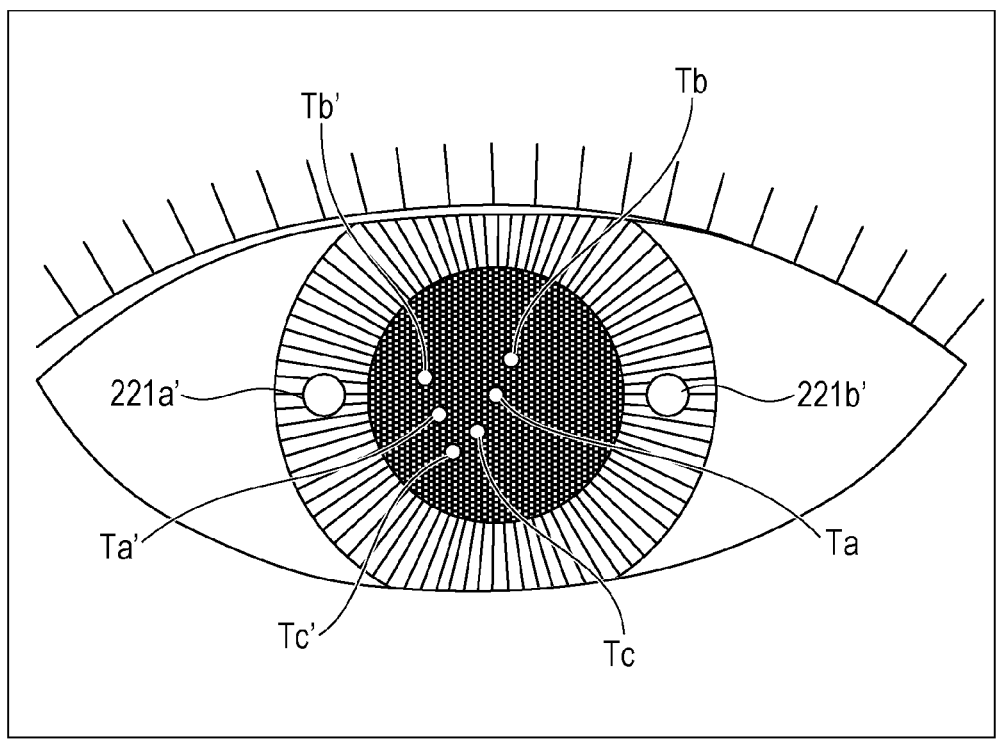
FIG. 7 is a diagram illustrating the anterior ocular segment image of the cornea bright spot in an IOL-implanted eye.

FIG. 7 illustrates the anterior ocular segment image imaged by the imaging device 220 for an IOL-implanted eye. The cornea bright spot image is formed by the imaging device 220 as the index images Ta, Tb, and Tc as described previously, and cornea bright spot ghosts reflected by the IOL 601 are formed by the imaging device 220 as index images Ta', Tb', and Tc'.

As the corneal vertex and the vertex for IOL 601 are not on the same axis, and the inclination of the cornea Ef and the IOL 601 are different, the IOL reflection ghost reflected by the IOL 601 is the index image Ta' that deviates from the index image Ta, which is the cornea bright spot image, horizontally and vertically depending on the state of the IOL 601. As illustrated in FIG. 6, the IOL reflection ghost reflected by the IOL 601 forms an image at a position near the cornea Ef, which becomes the index images Ta', Tb', and Tc' inclined to the left in comparison with the index images Ta, Tb, and Tc, which are the cornea bright spot images.

If auto-alignment is performed based on the IOL reflection ghost index images Ta', Tb', and Tc', the auto-alignment will complete at a position deviating from the subject eye E at the X, Y, and Z positions.

By selecting the cornea bright spot image index images, false detections of the index images using auto-alignment of the IOL reflection ghost index images is prevented. Therefore, auto-alignment can be properly performed.

Figure 8:
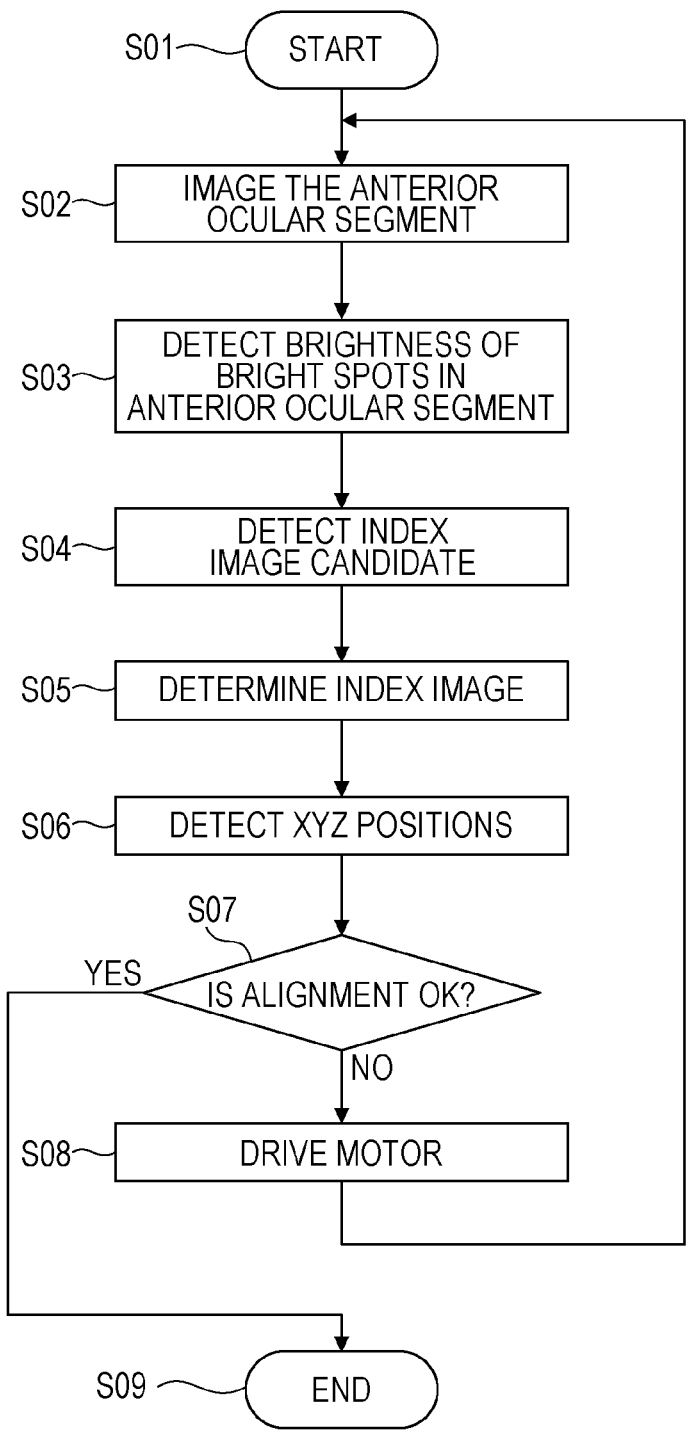
FIG. 8 is a flowchart describing the alignment method related to an embodiment of the present invention.

FIG. 8 is a flowchart of the auto-alignment in which the cornea bright spot image index images are selected. A computer program for executing this processing is stored in the program storage unit 491 in the system control unit 401 beforehand. The calculation processing 494 in the system control unit 401 reads and executes this computer program from the program storage unit 491. As a result, the processing illustrated below is achieved.

As a step S01, this auto-alignment processing starts. After this auto-alignment has started, the examiner has the subject rest their chin on the chinrest 112, and adjusts the chinrest 112 with the chinrest drive mechanism 113 so that the position of the subject eye E in the Y-axis direction reaches a predetermined height. Specifically, the examiner operates the joystick 101 to move the position of the measuring unit 110 so that the cornea image of the subject eye E is displayed in the LCD monitor 116. Afterwards, the examiner pushes the measurement start switch 404. Once the measurement start switch 404 is pushed, the system control unit 401 starts the auto-alignment.

At a step S02, the system control unit 401 controls the light source drive circuit 412 to light the eye refraction measuring light source 201, which is an example of a first projecting unit, and project a light beam on the subject eye E. The imaging device 220 images the anterior ocular segment of the subject eye E by detecting the light beam reflected from the projected light beam by the subject eye E. The imaged anterior ocular segment image is stored in the memory 408. The remainder of the auto-alignment optical system is constructed by the eye refraction measuring light source 201, the imaging device 220, and any associated configurations.

Figure 9:
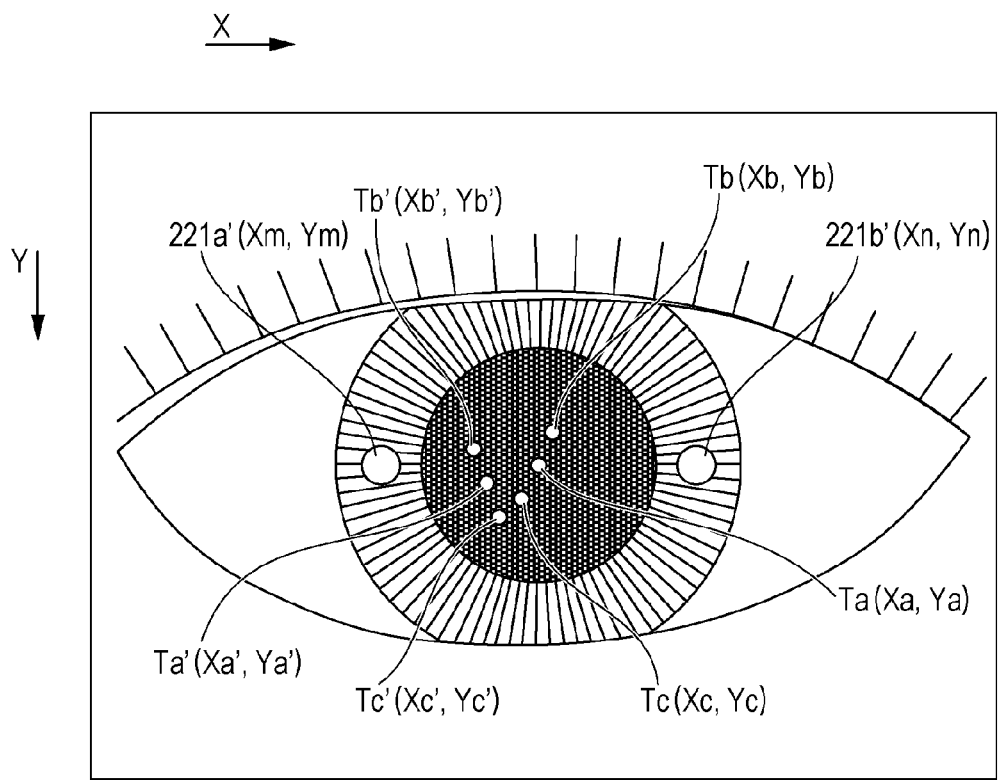
FIG. 9 is a diagram illustrating a cornea bright spot selection method for IOL-implanted eyes.

At a step S03, the system control unit 401 detects the cornea reflection bright spot images 221a' and 221b' from the anterior ocular segment image of the subject eye E stored in the memory 408 by the anterior ocular segment lighting light sources 221a and 221b, which are second projecting units. FIG. 9 is a diagram schematically an example of the anterior ocular segment image of the subject eye E stored in the memory 408. The system control unit 401 calculates the center positions (CX, CY) of the detected cornea reflection bright spot images 221a' and 221b'. The following expression (1) is used for this calculation.

$$(CX,CY)=((Xm+Xn)/2,(Ym+Yn)/2) \qquad \text{Expression (1)}$$

At a step S04, the system control unit 401 detects the three index images, which are formed by the light beam divided by the alignment prism 223, from the anterior ocular segment image of the subject eye E stored in the memory 408. As candidates for the cornea bright spot image index images, the cornea bright spot image index images Ta, Tb, and Tc and the IOL reflection ghost index images Ta', Tb', and Tc' are detected. The detection of multiple bright spot images based on the reflected light beam from the subject eye E is executed in a module region, which is an example of a detecting unit, in the system control unit 401.

The index images Tb and Tc divided by the alignment prism 223 are positioned at a predetermined height and horizontal position relative to the index image Ta, which enables detection by limiting the detection range.

An example of the cornea bright spot image detection method will now be illustrated.

As a first step, the center bright spot image from the cornea bright spot image (index image Ta) is detected.

As a second step, the upper bright spot image (index image Tb) is detected. The upper bright spot image (index image Tb) is positioned at a predetermined height and horizontally within a predetermined range relative to the center bright spot image (index image Ta), which enables detection by limiting the detection range.

As a third step, the lower bright spot image (index image Tc) is detected. The lower bright spot image (index image Tc) is positioned on a straight line that passed through the upper bright spot image (index image Tb) and the center bright spot image (index image Ta), and is positioned at a predetermined height in relation to the upper bright spot image (index image Tb). For this reason, detection is enabled by limiting the detection range.

At the first step, index images Tb and Tc are also detected as candidates for the center bright spot image from the cornea bright spot image. However, when the index image Tb or the index image Tc is detected as a candidate for the center bright spot image, the upper bright spot image and the lower bright spot image is not detected at the second step and the third step. For this reason, when the upper bright spot image is not detected at the second step, or the lower bright spot image is not detected at the third step, the system control unit 401 determines the bright spot image detected at the first step is not the center bright spot image (index image Ta). Therefore, when the index image Ta is detected as the center bright spot image, the index images Tb and Tc are not detected as the center bright spot image.

By using such a detection method, the three cornea bright spot images (index images) can be detected with a high level of accuracy.

At a step S05, the system control unit 401 performs a determination on which of the multiple index images, which are cornea bright spot images, is to be used for auto-alignment.

As described beforehand, the IOL reflection ghost index image Ta' (Xa', Ya') appears at positions of varying X coordinates and Y coordinates depending on the state of the IOL 601 and the cornea bright spot image index image Ta (Xa, Ya). Center points C of the index image Ta and the cornea reflection bright spot images 221a' and 221b' from the anterior ocular segment lighting light sources 221a and 221b are also images reflected by the cornea. The anterior ocular segment lighting light sources 221a and 221b are arranged so these center points have the same position. For this reason, a distance D between the center point C and the cornea bright spot image index image Ta is less than a distance D' of the center point C and the IOL reflection ghost index image Ta' (D<D'). The system control unit 401 calculates the distance from the center point C for each of the multiple detected index images and compares the calculated distances. The system control unit 401 determines to use the index image closest to the center point C for auto-alignment. The system control unit 401, which is an example of a selecting unit, selects the index image to use for auto-alignment from multiple index images in this way. The distance D between the center point C and the cornea bright spot image index image Ta, and the distance D' between the center point C and the IOL reflection ghost index image Ta' is calculated by the following expressions (2) and (3).

$$D=((CX-Xa)^2+(CY-Ya)^2)^{1/2} \qquad \text{Expression (2)}$$

$$D'=((CX-Xa')^2+(CY-Ya')^2)^{1/2} \qquad \text{Expression (3)}$$

At a step S06, the system control unit 401 calculates the XY-axis directional position for the selected cornea bright spot image index image Ta (Xa, Xb). The system control unit 401 calculates the Z-axis directional position from the difference in the X coordinates (Xb-Xc) of the cornea bright spot image index images Tb and Tc. The system control unit 401 then calculates the deviation between the calculated XYZ-axis directional positions and the optical axis (image center) regarding the XY-axis directions, and calculates the amount of deviation from the proper distance regarding the Z-axis direction. This processing is executed in the system control unit 401 in a module region, which is an example of a calculating unit, configured to calculate the state of alignment between the subject eye and the optical system from the multiple detected bright spot images.

At a step S07, the system control unit 401 determines whether or not the XYZ positions calculated at the step S06 are within the allowable range to complete alignment (within the allowable range defining that the state of alignment is in a proper state). If within the range, the system control unit 401 decides to complete the auto-alignment. When the XYZ positions are not within the allowable range to complete auto-alignment, processing proceeds to a step S08.

At a step S08, the system control unit 401 controls the motor drive circuit 413 to drive the X-axis drive motor 103, the Y-axis drive motor 104, and the Z-axis drive motor 108 in the XYZ directions for the amount of deviation in the XYZ directions calculated at the step S06. After driving these motors, processing returns to the step S02, and the processing from the step S02 is performed. This processing is repeated until it has been determined that alignment is complete at the step S07.

When the displaying the calculated state of alignment, the system control unit 401 displays the amount of deviation calculated at the step S06 (distance from the current position to the position at which the proper state is achieved) on the LCD monitor 116 as the state of alignment.

As previously described, according to the present embodiment, when the subject eye E is an IOL-implanted eye, the actual cornea bright spot image index image that is not an IOL reflection ghost can be correctly selected. For this reason, the time and effort to perform alignment can be reduced. Therefore, strain on the examiner and the subject can be reduced during measurement. By using correctly selected cornea bright spot image index images for auto-alignment, automatic alignment (auto-alignment) can be properly performed on subject eyes implanted with an IOL. That is to say, false detections of IOL reflection ghost index images can be prevented, and auto-alignment can be completed correctly.

According the previously described embodiment, selection was performed by the distance between the center point C and the X and Y coordinates, but selection may also be performed by only the X coordinate or the Y coordinate. Selection may also be performed by setting a predetermined range from the center point C, and determining whether or not the index image Ta, which is the center of the cornea bright spot image, is within this range.

According to the aforementioned description, a case is assumed in which only one IOL reflection ghost occurs, but the same effect can be obtained even for cases in which multiple IOL reflection ghosts occur.

While an embodiment of the present invention has been described in detail, the embodiment only serves as a specific example to illustrate an implementation of the present invention. The technical scope of the present invention is not limited to the embodiment. Various modifications may be made to the present invention without departing from the scope of the present invention, and these are included in the technical scope of the present invention.

For example, regarding the embodiment, an eye refractometer has been illustrated as an example of the ophthalmic device, but the ophthalmic device is not restricted to an eye refractometer. Regarding the present invention, ophthalmic measuring devices other than an eye refraction measuring device such as an ophthalmic photographing device, an ocular axial length measuring device, optical coherence tomography (OCT), etc., are applicable to the IOL eye selection according to the present invention, as long as the device is capable of transillumination observation.

Other Embodiments

Embodiments of the present invention can also be realized by a computer of a system or apparatus that reads out and executes computer executable instructions recorded on a storage medium (e.g., transitory or non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-086878, filed Apr. 17, 2013, which is hereby incorporated by reference herein in its entirety.

What is claimed is:

1. An ophthalmic device comprising:
a measuring unit configured to measure information of a subject eye;
a first projecting unit configured to project a light beam onto the subject eye in a first direction;
a second projecting unit configured to project a light beam onto the subject eye from a second direction different from the first direction;
a selecting unit configured to select a bright spot image corresponding to the light beam which is projected by the first projecting unit and is reflected by the cornea of the subject eye from among a plurality of first bright spot images on the basis of a positional relationship between the first bright spot image and a second bright spot image corresponding to the light beam projected from the second projecting unit, the plurality of first bright spot images including a bright spot image corresponding to the light beam which is projected by the first projecting unit and is reflected by the cornea of the subject eye and a bright spot image corresponding to the light beam which is projected by the first projecting unit and is reflected by a portion other than the cornea of the subject eye; and
a calculating unit configured to calculate a state of alignment between the subject eye and the measuring unit using the bright spot image selected from the plurality of first bright spot images.

2. The ophthalmic device according to claim 1,
wherein the second projecting unit is configured to project a light beam to two symmetrical locations in relation to an optical path for the light beam projected by the first projecting unit; and
wherein the selecting unit is configured to select the first bright spot image in a position near the center of two of the second bright spot images as the reflected light beam reflected by the cornea of the subject eye.

3. The ophthalmic device according to claim 1, further comprising:
a deflecting unit configured to divide the reflected light beam from the light beam projected by the first projecting unit into a plurality of reflected light beams to be deflected in different directions, and change the relative positions of the plurality of first bright spot images formed by the divided plurality of reflected light beams depending on the distance between the subject eye and the measuring unit;

wherein the measuring unit is located at a suitable distance to the subject eye for measuring the subject eye when the relative positions of the plurality of first bright spot images formed by the divided plurality of reflected light beams are at predetermined positions;

and wherein the calculating unit is configured to calculate the distance between the measuring unit and the subject eye as the state of alignment on the basis of the relative positions of the plurality of first bright spot images formed by the plurality of reflected light beams deflected by the deflecting unit.

4. The ophthalmic device according to claim 3, wherein the deflecting unit comprises an alignment prism diaphragm including a plurality of alignment prisms configured to deflect the reflected light beam into the different directions.

5. The ophthalmic device according to claim 1, further comprising:
a detecting unit configured to detect first bright spot images, and a second bright spot image.

6. The ophthalmic device according to claim 1, further comprising:
a drive unit configured to drive the measuring unit; and
an auto-alignment unit configured to perform alignment with the subject eye by controlling the drive unit based on the state of alignment calculated by the calculating unit.

7. The ophthalmic device according to claim 1, wherein the measuring unit is operable to measure information of an IOL-implanted eye implanted with an artificial lens as the subject eye.

8. The ophthalmic device according to claim 1, further comprising:
a display unit configured to display the direction of movement from the state of alignment calculated by the calculating unit to a proper state of alignment for the measuring unit.

9. A control method for an ophthalmic device including a measuring unit to measure information of a subject eye, the method comprising:
projecting a first light beam onto the subject eye in a first direction;
projecting a second light beam onto the subject eye by a second projecting unit from a direction different from the first direction;
selecting a bright spot image corresponding to a reflected light beam reflected by the cornea of the subject eye from among a plurality of first bright spot images on the basis of a positional relationship between the first bright spot image and a second bright spot image corresponding to the second light beam, the plurality of first bright spot images including a bright spot image corresponding to the reflected light beam reflected by the cornea of the subject eye and a bright spot image corresponding to a reflected light beam reflected by a portion other than the cornea of the subject eye; and
calculating a state of alignment between the subject eye and the measuring unit using the bright spot image, reflected light beam reflected by the cornea of the subject eye, selected from the plurality of first bright spot images.

10. The control method for an ophthalmic device according to claim 9,
wherein a light beam is projected to two symmetrical positions in relation to the optical path for the first light beam during projection of the second light beam; and
wherein the first bright spot image in a position near the center of two of the second bright spot images is selected as the reflected light beam reflected by the cornea of the subject eye during the selecting step.

11. The control method for an ophthalmic device according to claim 9, further comprising:
dividing the reflected light beam from the first light beam into a plurality of reflected light beams to be deflected in different directions;
changing the relative positions of the plurality of first bright spot images formed by the divided plurality of reflected light beams depending on the distance between the subject eye and the measuring unit; and
calculating the distance between the measuring unit and the subject eye as the state of alignment on the basis of the relative positions of the plurality of first bright spot images formed by the plurality of reflected light beams deflected by the deflecting unit;
wherein the measuring unit is at a suitable distance to the subject eye for measuring the subject eye when the relative positions of the plurality of first bright spot images formed by the divided plurality of reflected light beams are at predetermined positions.

12. The control method for an ophthalmic device according to claim 11, further comprising:
deflecting the plurality of reflected light beams using an alignment prism diaphragm including a plurality of alignment prisms to deflect the reflected light beam into different directions.

13. The control method for an ophthalmic device according to claim 9, further comprising:
detecting first bright spot images, and a second bright spot image.

14. The control method for an ophthalmic device according to claim 9, further comprising:
performing alignment with the subject eye by controlling a drive unit which is operable to drive the measuring unit, based on calculation results of the calculated state of alignment.

15. The control method for an ophthalmic device according to claim 9,
wherein the measuring unit is operable to measure an IOL-implanted eye implanted with an artificial lens as the subject eye.

16. The control method for an ophthalmic device according to claim 9, further comprising:
displaying the direction of movement from the state of alignment calculated during the calculating step to the proper state of alignment for the measuring unit on a display.

17. A non-transitory computer readable medium storing, in a non-transient manner, a program containing processor executable instructions which upon execution cause one or more processors to execute the control method for an ophthalmic device according to claim 9.

18. The ophthalmic device according to claim 1,
wherein the second projecting unit is configured to project a light beam to at least two locations; and
wherein the selecting unit is configured to select the first bright spot image in a position near the center of the at least two of the second bright spot images as the reflected light beam reflected by the cornea of the subject eye.

19. The control method for an ophthalmic device according to claim 9,
- wherein a light beam is projected to at least two positions in relation; and
- wherein the first bright spot image in a position near the center of the at least two of the second bright spot images is selected as the reflected light beam reflected by the cornea of the subject eye during the selecting step.

20. An ophthalmic device comprising:
- a measuring unit configured to measure information of a subject eye;
- a first projecting unit configured to project a light beam onto the subject eye in a first direction;
- a second projecting unit configured to project a light beam onto the subject eye from a second direction different from the first direction;
- an imaging device configured to pick up a plurality of first bright spot images corresponding to the light beam projected by the first projecting unit and reflected by the subject eye and at least two second bright spot images corresponding to the light beam projected by the second projecting unit and reflected by the subject eye; and
- an alignment unit configured to perform alignment of the subject eye and the measuring unit by using, among the plurality of first bright spot images picked up by the imaging device, a first bright spot image near the center of the at least two second bright spot images.

21. The ophthalmic device according to claim 20,
- wherein the plurality of first bright spot images includes a bright spot image corresponding to a light beam reflected by a cornea of the subject eye and a bright spot image corresponding to a light beam reflected by a portion other than the cornea of the subject eye.

22. The ophthalmic device according to claim 21,
- wherein the subject eye is a subject eye that includes an artificial lens; and
- wherein, among the plurality of first bright spot images, the bright spot image corresponding to the light beam reflected by the portion other than the cornea of the subject eye is a bright spot image corresponding to a light beam reflected by the artificial lens.

* * * * *